United States Patent [19]
Teh et al.

[11] Patent Number: 5,799,700
[45] Date of Patent: Sep. 1, 1998

[54] AUTOMATIC INTRAVENOUS FLOW CONTROL DEVICE

[76] Inventors: Eutiquio L. Teh, 2440 Tiebout Ave., #2, Bronx, N.Y. 10458; William L. Teh, 134-A Kaimito Road, Kalookan City MM 1400, Philippines

[21] Appl. No.: 671,374

[22] Filed: Jun. 27, 1996

[51] Int. Cl.$^6$ ............................................. F15D 1/02
[52] U.S. Cl. ............................................. 138/45; 138/46
[58] Field of Search ............................ 138/40, 45, 46, 138/104

[56] References Cited

U.S. PATENT DOCUMENTS

| | | | |
|---|---|---|---|
| 934,286 | 9/1909 | Cole | 137/517 |
| 1,657,663 | 1/1928 | Devereux | 138/45 |
| 2,124,580 | 7/1938 | Lavine | 138/45 |
| 2,245,271 | 6/1941 | Guill | 251/144 |
| 2,632,476 | 3/1953 | Miller | 138/45 |
| 2,899,979 | 8/1959 | Dahl et al. | 138/45 |
| 3,109,426 | 11/1963 | Noonan et al. | 128/240 |
| 3,367,362 | 2/1968 | Hoffman | 138/45 |
| 3,970,105 | 7/1976 | Pelton et al. | 138/45 |
| 4,324,239 | 4/1982 | Gordon et al. | 128/214 R |
| 4,344,459 | 8/1982 | Nelson | 138/45 |
| 4,361,147 | 11/1982 | Aslanian et al. | 128/214 |
| 4,429,856 | 2/1984 | Jackson | 251/149.1 |
| 4,497,468 | 2/1985 | Hubbard et al. | 251/117 |
| 4,957,483 | 9/1990 | Gonser et al. | 604/30 |
| 5,019,055 | 5/1991 | O'Boyle | 604/249 |
| 5,323,806 | 6/1994 | Watari et al. | 138/45 |
| 5,514,110 | 5/1996 | Teh | 604/247 |

FOREIGN PATENT DOCUMENTS

| | | | |
|---|---|---|---|
| 649238 | 9/1962 | Canada | 138/45 |

*Primary Examiner*—Stephen F. Gerrity
*Attorney, Agent, or Firm*—Fitzpatrick, Cella, Harper & Scinto

[57] ABSTRACT

An IV fluid flow control device includes a rigid casing defining a flow passage having a fluid entrance and a fluid exit. A rigid, previous base is affixed inside the flow passage of the casing. A flexible, resilient flow regulator is disposed inside the flow passage of the casing adjacent to and upstream of the base. The flow regulator normally has a smaller cross-section than does the flow passage, leaving open space for fluid to pass. A rigid, previous cap is disposed inside the flow passage of the casing adjacent to and upstream of the flow regulator. The cap is axially movable inside the flow passage of the casing. The flow regulator biases the cap against pressure from fluid entering through the fluid entrance. Increases beyond a threshold level in the pressure from fluid entering through the fluid entrance cause axial compression of the flow regulator, thereby expending the transverse cross-section of the flow regulator, resulting in a reduction of the open space for fluid to pass. The reduction of the open space will impede an increase in the flow rate through the fluid exit even if the pressure from fluid entering through the fluid entrance is increased.

16 Claims, 6 Drawing Sheets

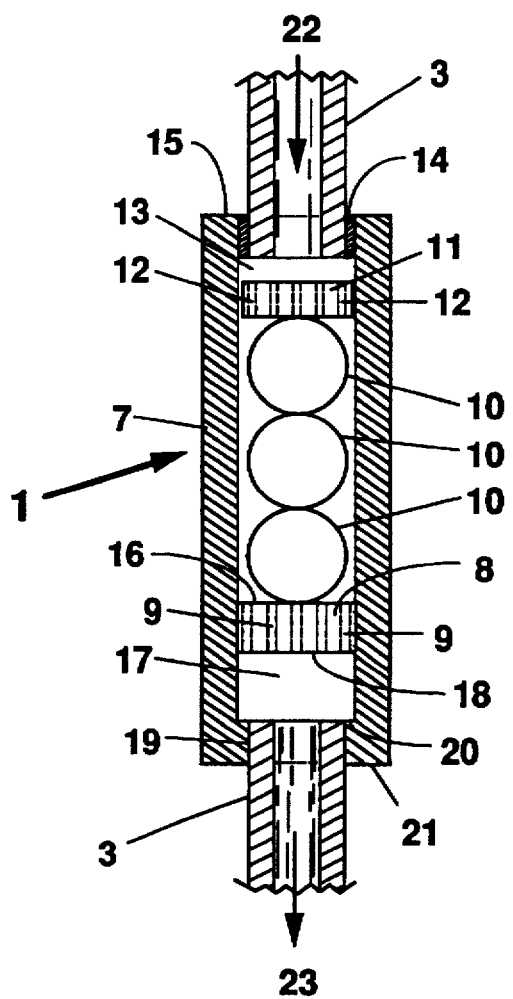
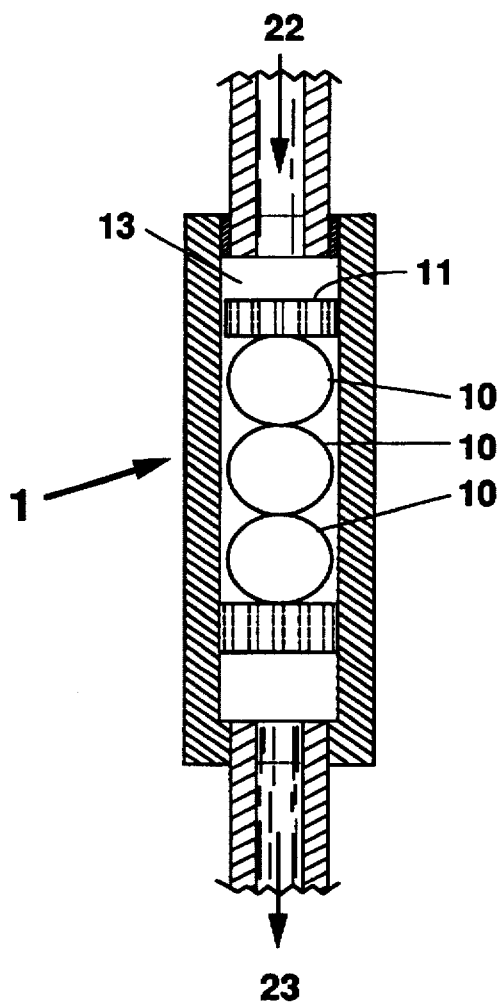
FIG. 4a  FIG. 4b

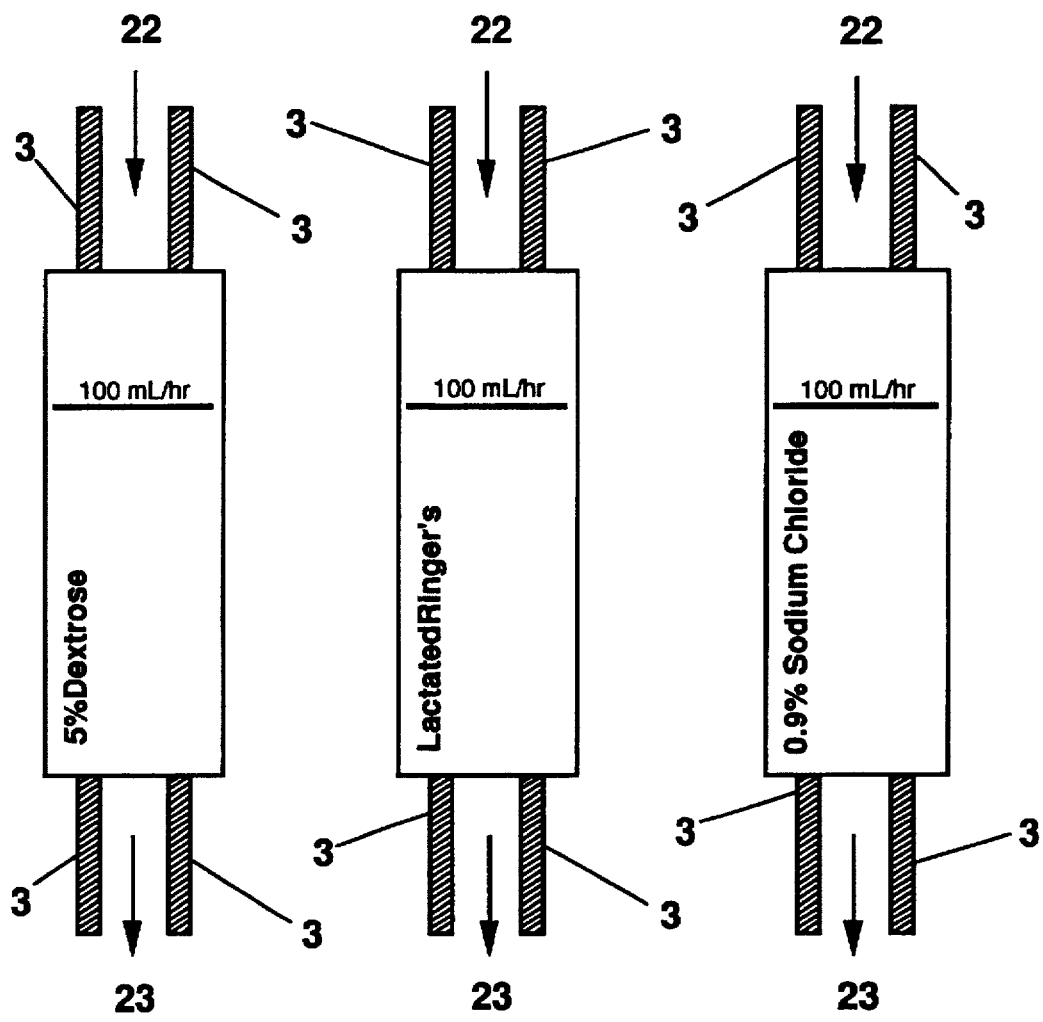

1
AUTOMATIC INTRAVENOUS FLOW CONTROL DEVICE

BACKGROUND OF THE INVENTION

1. Field of the Invention

The present invention relates to an inexpensive automatic intravenous flow control device.

2. Description of the Prior Art

Devices are known for controlling the flow of intravenous (IV) fluids to a patient. For example, infusion pumps may be used to control the flow of IV fluids to a patient within 10–20% of the prescribed infusion rate. However, infusion pumps are bulky, expensive, and require periodic maintenance.

Simple clamps may be applied to the IV line and may provide acceptable flow control in certain non-critical circumstances. The desired IV drip rate is determined by adjusting the clamp at the beginning of the IV infusion, but must be checked regularly. Because drop size varies with the viscosity of the IV fluid, the drip rate required to give a predictable rate of the infusion will vary from solution to solution. Also, changes in the height of the fluid level in the IV container relative to the patient (for example, when the patient sits up or gets out of bed or as the fluid level in the IV container falls) result in changes in the drip rate. This device may be inexpensive but it lacks safety and accuracy.

Variable resistance devices (e.g., Dial-A-Flow by Abbott Laboratories) may also be used as an integral part of the IV line. This device is also sensitive to viscosity changes and requires a constant hydrostatic pressure to maintain constant flow and therefore is subject to the same inaccuracies as the simple clamp discussed above. These devices can be recalibrated for solutions of known viscosity, but such a minor advantage probably fails to justify the increased expense of such devices for routine use.

Gravity-fed pressure-compensating devices (e.g., Isoflux by Geistlich) may also be used to control IV flow. This device has a flexible diaphragm that partially compensates for changes in hydrostatic and venous pressures. While the rate of infusion is more constant and therefore more accurate than the simple clamp, these devices are quite expensive.

Electronic gravity-fed controllers (e.g., Accudot by Imed) are flow control devices that use a variable resistor that is incorporated into the IV set and is adjusted automatically by an electronic controller. Because the controller monitors the drip rate, the infusion rate also varies from solution to solution. However, the rate of flow is not affected by changes in patient position or venous pressure. Again, while the infusion rate is relatively accurate, these controllers are quite expensive.

U.S. Pat. No. 4,361,147 discloses a flow control device for administering IV fluids wherein the fluid flow may be controlled by a spring-biased fluid control cam. Again, such a device is quite expensive to produce.

U.S. Pat. No. 4,324,239 discloses a safety valve for catheterization procedures wherein a piston having an internal flow path is biased by a resilient member such that as fluid increases in the valve, fluid flow through valve also increases. Such a device would be unusable to provide a relatively constant fluid flow through an IV flow controller.

U.S. Pat. No. 5,514,110 (issued May 7, 1996 to one of the present applicants) discloses an IV flow control device in which a casing has a flow-restricting base through which a hollow pin is disposed. The pin has flange on its upstream and, an elongated opening on its side, and an exit opening on its downstream end. The pin is biased against the incoming fluid. As the pressure increases, the pin will be forced downstream through the base, progressively blocking off more of the pin's side opening, impeding increases in fluid flow. This device works well, is easy to make and use, and is inexpensive, but the design employs a separate biasing means not required in the present invention.

Thus, what is needed is an inexpensive, compact, easy-to-manufacture, easy-to-use IV fluid flow controller that can provide accurate control of fluid flow into the patient. Such a device should be able to be incorporated as an integral part of the IV infusion set so as not to be easily removable.

SUMMARY OF THE INVENTION

An object of the present invention is to provide an inexpensive, easy-to-operate IV fluid flow control device which can accurately control the flow of a fluid into a patient.

According to one aspect of the present invention, an IV fluid flow control device includes a rigid casing defining a flow passage having a fluid entrance and a fluid exit. A rigid, previous base is affixed inside the flow passage of the casing. A flexible, resilient flow regulator is disposed inside the flow passage of the casing adjacent to and upstream of the base. The flow regulator normally has a smaller cross-section than does the flow passage, leaving open space for fluid to pass. A rigid, previous cap is disposed inside the flow passage of the casing adjacent to and upstream of the flow regulator. The cap is axially movable inside the flow passage of the casing. The flow regulator biases the cap against pressure from fluid entering through the fluid entrance. Increases beyond a threshold level in the pressure from fluid entering through the fluid entrance cause axial compression of the flow regulator, thereby expanding the transverse cross-section of the flow regulator, resulting in a reduction of the open space for fluid to pass. The reduction of the open space will impede an increase in the flow rate through the fluid exit even if the pressure from fluid entering through the fluid entrance is increased.

The flow regulator may be a plurality of spheres. The greater the pressure exerted on the spheres, the greater the spheres' transverse expansion and therefore the greater the reduction of the total space available for fluid to pass, thereby causing a greater reduction in fluid flow. If the pressure is high enough, the balls will actually clog the system and cause fluid flow to stop. This is the safety feature of the device.

BRIEF DESCRIPTION OF THE DRAWINGS

The advantageous features according to the present invention will be more readily understood from the following detailed description of the preferred embodiments when taken in conjunction with the attached drawings, in which like numerals reference similar elements:

FIGS. 4a–4d schematically depict the operation of the FIG. 3 device;

FIGS. 5a–5c depict the outside of the FIG. 3 device for different solutions;

DETAILED DESCRIPTION OF THE PREFERRED EMBODIMENTS

Figures 1, 2:
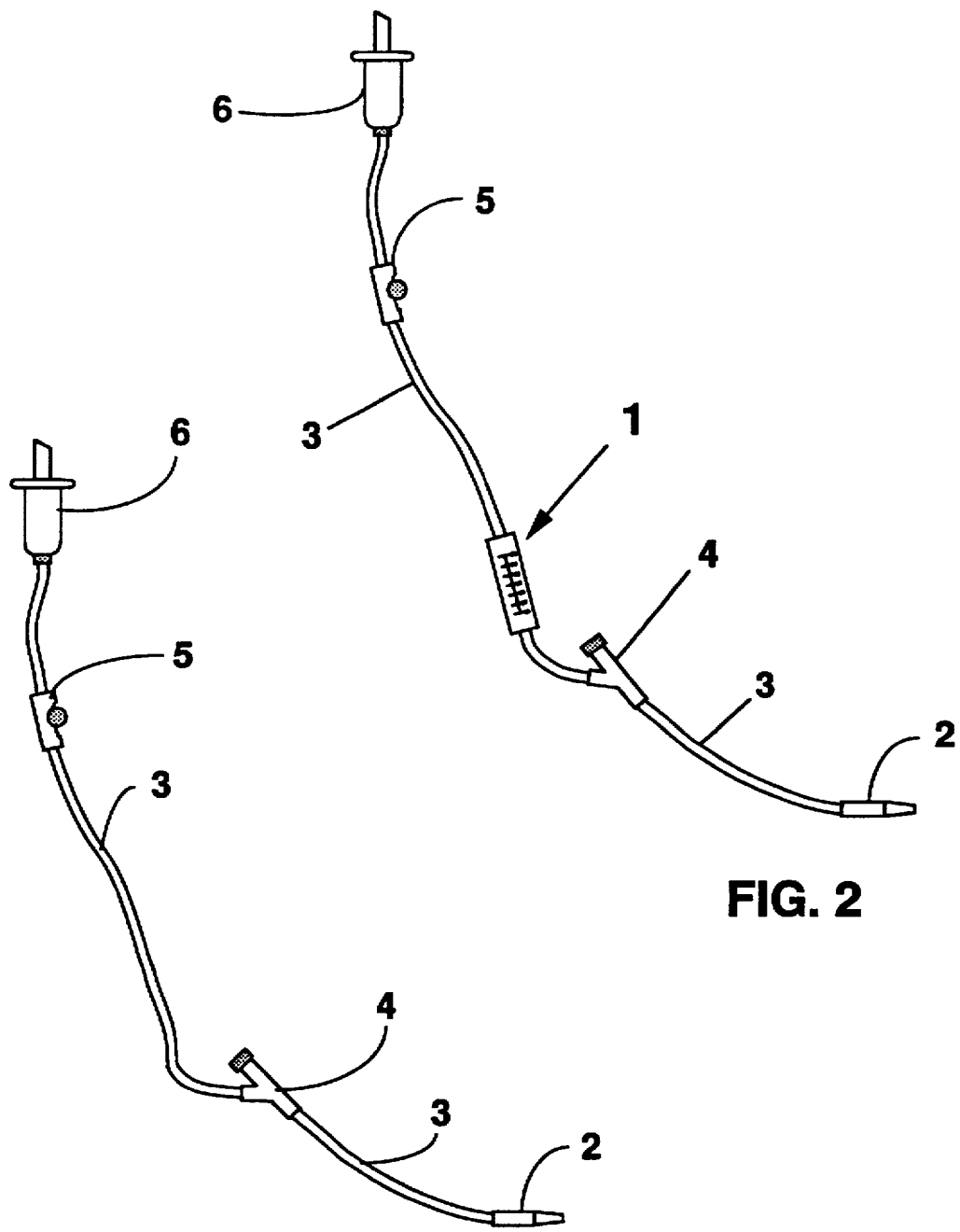
FIG. 1 is a schematic drawing of a prior art IV infusion set such as a "Venoset 78"
FIG. 2 is a schematic drawing of an IV infusion set incorporating the automatic flow control device according to the present invention.

FIG. 1 depicts a prior art IV infusion set such as a "VENOSET 78" in which IV fluid enters a drip chamber 6, passes through a manual flow control device 5, passes down plastic IV tubing 3, through the Y-injection site 4 and to the male adaptor 2 which is coupled to a venipuncture device (not shown).

FIG. 2 shows the automatic flow control device 1 according to the present invention installed in the FIG. 1 IV set between the Y-injection site 4 and the manual control device 5.

Figure 3:
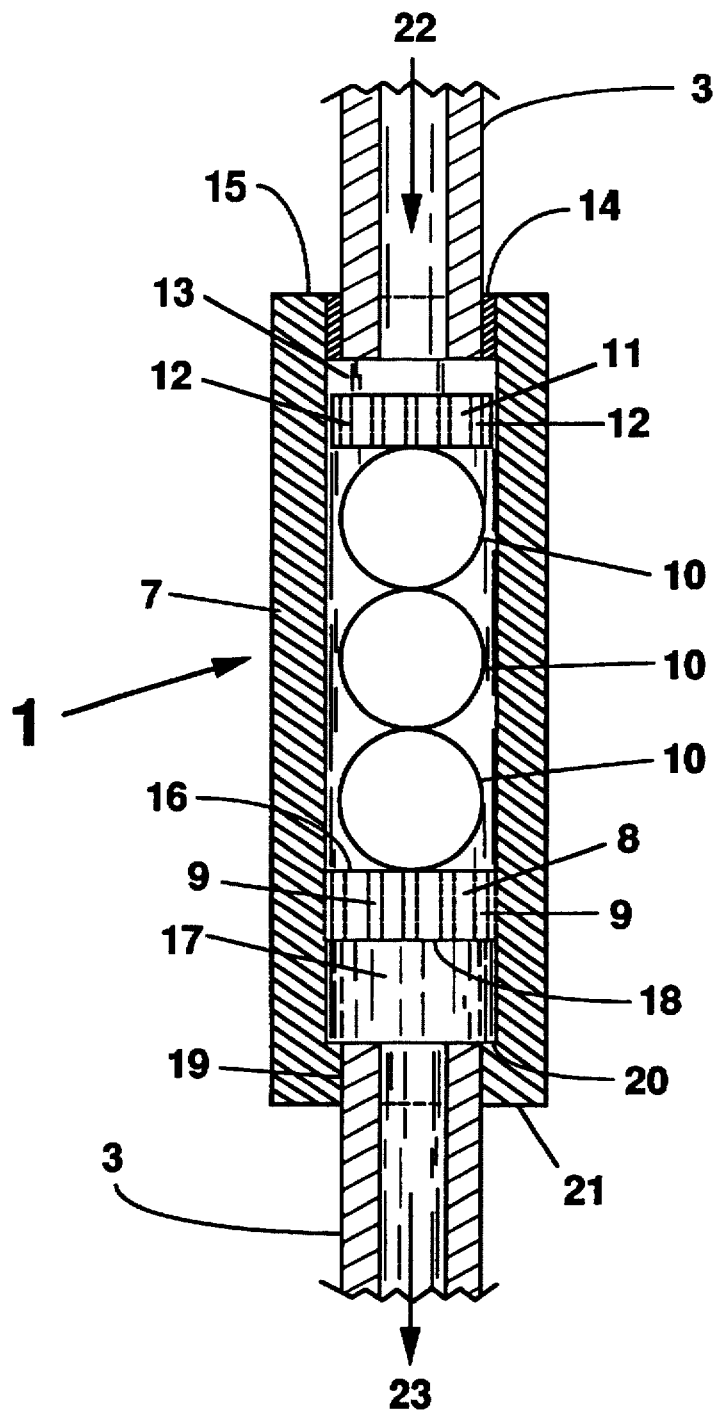
FIG. 3 is a schematic partial cross-section of the preferred embodiment according to the present invention.

FIG. 3 shows the preferred embodiment according to the present invention wherein the flow control device 1 is coupled to IV plastic tubing 3. The device 1 has a rigid, transparent casing 7 preferably made of a plastic generally similar to those materials used in the art in the construction of the male adaptor 2. The casing 7 has three bores or chambers. Bore 13 starts from the top 15 of the casing 7 and ends at the top 16 of base 8. Bore 17 starts from the bottom 18 of base 8 and ends at shoulder 20. A slightly smaller bore 19 that is connected to bore 17 starts from shoulder 20 and ends at bottom 21 of casing 7. The diameter of smaller bore 19 is made suitable for coupling with tubing 3. A diameter reducer 14 shaped as a hollow cylinder and preferably made of plastic similar to the material used in the construction of the casing 7 is circumferentially attached to the uppermost portion of the casing 7. Tubing 3 is then attached to the reducer 14. The method of attaching reducer 14 to casing 7 and tubing 3 to reducer 14 may be any of those well known in the art for use in attaching tubing 3 to other elements in the system, such as male adaptor 2. Casing 7 has a perforated base 8 disposed on an inside thereof. The base 8 is preferably unitary with the casing 7, but may be a separate piece of similar material affixed in place by any of a number of methods employed in the art. In either case, its total perforations are sufficient to pass a specific fluid at 3–5 times the intended flow rate of that specific fluid for a particular device 1.

One or more flexible balls 10 that will act as flow regulators are also disposed inside the casing 7. These balls 10 are made of elastic material such as rubber, plastic or silicon compound. In their natural state, the balls 10 are shaped as either solid spheres or hollow spheres similar to that of a balloon filled with gas or liquid and have a smaller radius than does the bore 13. These balls 10 are placed on top of the base 8, stacked on one another and capped with a light weight perforated plastic cylindrical cap 11. Like the balls 10, the cylindrical cap 11 has a smaller radius than does bore 13, allowing space for fluid to flow between the circumferential edge of cap 11 and the inner wall of the casing 7, and allowing the cap 11 to move axially within the casing 7 without frictionally engaging the inner walls of the casing 7. Similar to the base 8, the total area of perforations in cap 11 plus the open area between the circumferential edges of cap 11 and the inner wall of casing 7 is sufficient to pass a specific fluid at 3–5 times the intended flow rate of that specific fluid for a particular device 1. Thus, the area of fluid passages in cap 11 as well as in base 8 are not a factor in the design of device 1. What is critical in the design of a specific device 1 is the area of fluid passage between the edges of balls 10 and the inner wall of casing 7. Incoming fluid 22 flows into chamber 13 of device 1, contacts cap 11, passes through perforations 12 and through the open space between edges of cap 11 and the inner wall of casing 7, passes through open spaces between edges of balls 10 and inner wall of casing 7, through the perforations 9 of base 8, and exits the device 1 through the downstream opening 17 as exit fluid 23.

Cap 11 is biased against incoming fluid 22 by the balls 10. As will be described in more detail below, as the pressure of the incoming fluid 22 increases, balls 10 are compressed along the longitudinal direction of the casing 7, and their horizontal circumferences increase, causing a reduction in the open spaces between the edges of balls 10 and the inner wall of casing 7. Thus, once balls 10 are compressed, increasing pressure will not result in increased flow through the device 1.

Figure 4C:
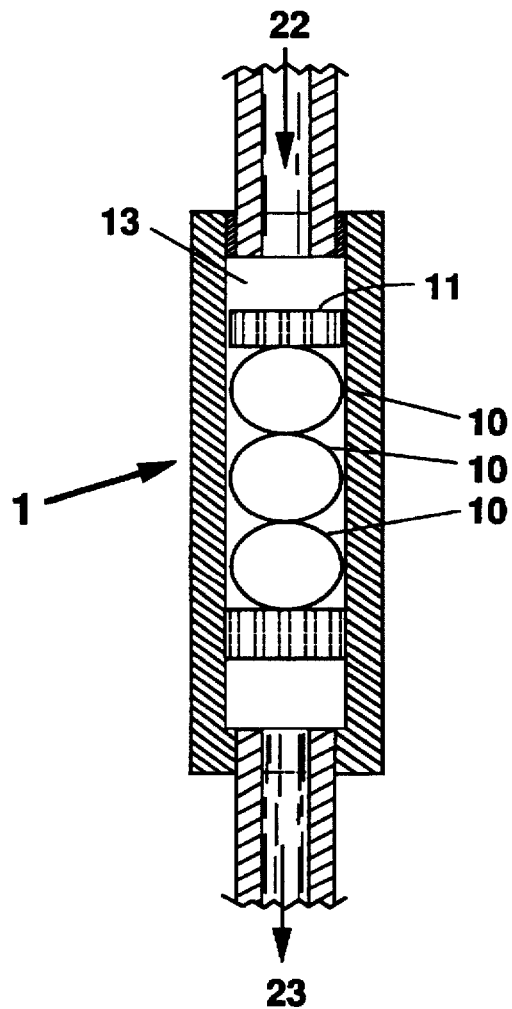

The above, briefly-described operation of the FIG. 3 embodiment is depicted more clearly in FIGS. 4a–4d. In FIG. 4a, laminar fluid flow or no fluid is flowing from the fluid entrance of device 1 and the balls 10 are at their normal conditions. FIGS. 4b and 4c illustrate increasing flow rates of incoming fluid 22, both of which exceed the calibrated maximum flow rate that will not compress the balls 10. These flow conditions shown in FIGS. 4b and 4c will cause pressure to build up in chamber 13 above the cap 11, exerting a downward pressure on the cap 11 and balls 10. As balls 10 are compressed and their horizontal circumferences increased, the open spaces between the edges of balls 10 and the inner wall of casing 7 are reduced, resulting in a reduction of fluid flows into the perforations of base 8 and to flow exit 23.

Figure 4D:
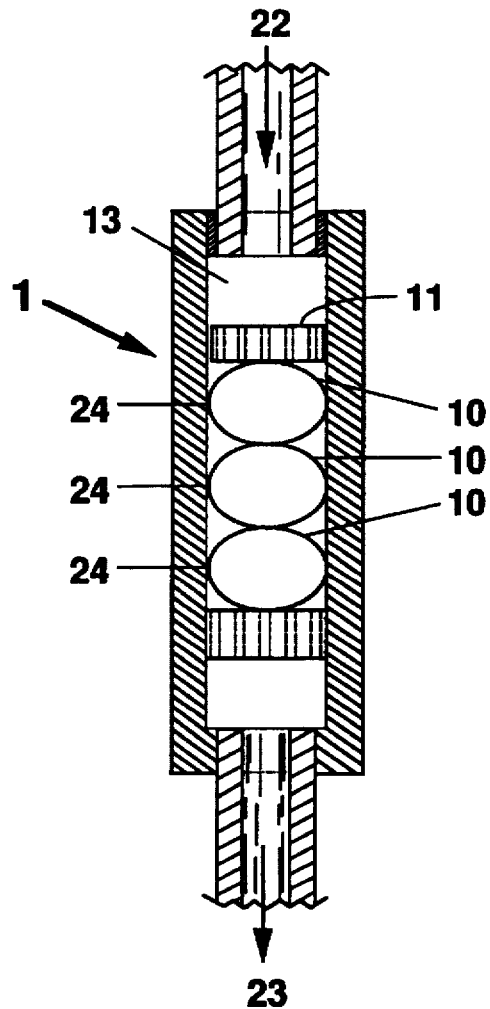

In FIG. 4d, the pressure on cap 11 and balls 10 is strong enough to compress the balls 10 and cause the edges of balls 10 to contact circumferentially with the inner wall of casing 7, thereby clogging the system and stopping the fluid flow. Contact points are shown as 24.

Preferably, the present invention may be provided for a wide variety of viscosities of IV fluids. That is, different sizes and/or different compressibility of the balls 10 may be designed depending upon the viscosity of the IV fluid and its projected flow rate. For example, FIG. 5a depicts a device 1 for 5% Dextrose solution at a rate of 100 ml/hr. FIG. 5b depicts a device 1 for Lactated Ringer's solution at a rate of 100 ml/hr. FIG. 5c depicts a device 1 for 0.9% Sodium Chloride solution at a rate of 100 ml/hr.

The design of a particular device 1 for a given solution must first consider the kind of solution to be infused. Because different infusion solutions have different viscosities, a particular device should only be used in the infusion of the solution for which the device was calibrated. Thus, it is preferred that calibration be carried out each particular infusion solution.

For practical purposes, the length of the device should not be more than 2–3 inches long. Therefore, if a wide range of infusion rates has to be calibrated for a particular solution, the marking of infusion rates as they appear on the outside surface of the casing 7 become very congested and difficult to read. For this, two or more sets of devices may be provided for adults and another set or two for children. As an example, a device with an infusion rate calibration of about 125 ml/hr will be designed for heavier adults, about 100 ml/hr for regular adults and about 50 ml/hr for children. A number of design parameters may be modified in order to calibrate the device for a particular flow rate. While it is possible to vary the inside diameter of the casing 7 it is more practical to design a fixed casing 7 and vary the size of balls 10 and/or their compressibility, which is defined as the increase in horizontal circumference per unit vertical pressure applied.

Figures 6A, 6B:
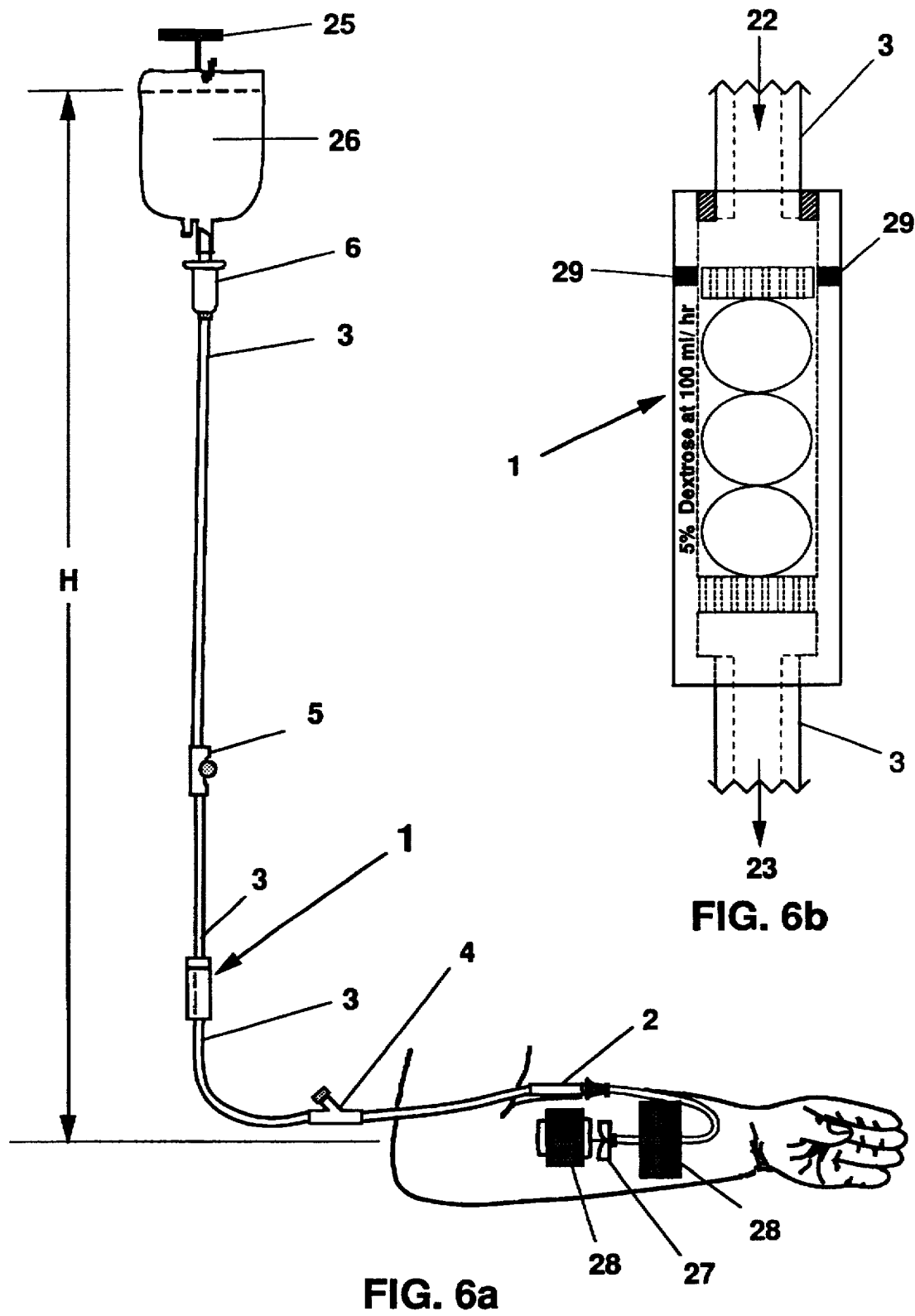
FIGS. 6a and 6b schematically depict the in-use operation of the FIG. 3 device.

FIG. 6a depicts a typical set-up for the automatic IV flow control device according to the present invention. The IV fluid bag 26 is supported from a support 25 at a height H of about 3-4 ft. above the venipuncture site. The fluid passes through drip chamber 6, line 3, Y-injection device 4, device 5 1 and then to male adaptor 2. Male adaptor 2 is coupled to venipuncture device 27, which transmits the fluid exiting adaptor 2 to an IV needle which is inserted in the patient's arm. As is well known, adhesive patches 28 secure the IV needle to the patient.

Referring to FIGS. 6a and 6b, the use of the embodiment of FIG. 3 will now be described. For example, suppose the patient is to be infused with 5% Dextrose solution at a rate of 100 ml/hr for 12 hours. First, a device 1 according to FIG. 5a will be chosen and is preferably inscribed or labeled 5% Dextrose-100 ml/hr on its container box. The manual flow control device 5 is closed and the IV container 26 is pierced and suspended about 3-4 feet above the venipuncture site. The drip chamber 6 is squeezed to establish proper fluid level (half full). Next, the manual flow control device 5 is opened to allow solution to expel air from the line after which the device 5 is again closed. A venipuncture is made to the patient and the male adaptor 2 is then attached to the venipuncture device 27. In a split of a second, the flow control device 5 is opened as much as possible so that the cap 11 will move downward (compressing the balls 10) and slightly below the 100 ml/hr line marking found on the outside surface of casing 7. The casing 7 should be translucent (or at least have a translucent window), so that the cap 11 will be visible for comparison against the marking line. Immediately after the cap 11 has moved, the flow control device 5 is then adjusted slowly back towards its closing direction so that the cap 11 will move back up and just coincides with the 100 ml/hr line marking 29. After device 5 has been set, infusion will then continue for 12 hours.

The individual components shown outline or designated by blocks in the attached drawings are all well known in the IV flow control arts, and their specific construction and operation are not critical to the operation or best mode for carrying out the invention.

While the present invention has been described with respect to what is presently considered to be the preferred embodiments, it is to be understood that the invention is not limited to the disclosed embodiments. To the contrary, the invention is intended to cover various modifications and equivalent arrangements included within the spirit and scope of the appended claims. For instance, the bores 13, 17, 19 could have non-circular cross-sections. The shape of the balls 10 could be modified accordingly. As an additional example, a different number of balls (including a single ball) could be employed. Also, instead of being perforated, the base 8 and the cap 11 could be porous. Accordingly, the scope of the following claims is to be accorded the broadest interpretation so as to encompass all such modifications and equivalent structures and functions.

What is claimed is:

1. An intravenous fluid flow control device comprising:

a rigid casing defining a flow passage having a fluid entrance and a fluid exit;

a rigid, previous base affixed inside said flow passage of said casing;

a flexible, resilient flow regulator disposed inside said flow passage of said casing adjacent to and upstream of said base, said flow regulator normally having a smaller transverse cross-section than does said flow passage, leaving open space for fluid to pass; and a rigid, previous cap disposed inside said flow passage of said casing adjacent to and upstream of said flow regulator, said cap being axially movable inside said flow passage of said casing, wherein said flow regulator biases said cap against pressure from fluid entering through said fluid entrance, wherein increases beyond a threshold level in the pressure from fluid entering through said fluid entrance cause axial compression of said flow regulator, thereby expanding the transverse cross-section of said flow regulator, resulting in a reduction of the open space for fluid to pass, so that the reduction of the open space will impede an increase in flow rate through said fluid exit even if the pressure from fluid entering through said fluid entrance is increased.

2. The device according to claim 1, wherein said casing comprises a transparent plastic having fluid flow calibration makings thereon.

3. The device according to claim 1, wherein said base is unitary with said casing.

4. The device according to claim 1, wherein said flow regulator is a solid sphere.

5. The device according to claim 1, wherein said flow regulator is a hollow sphere filled with fluid.

6. The device according to claim 1, wherein said flow regulator is made of rubber.

7. The device according to claim 1, wherein said flow regulator is made of plastic.

8. The device according to claim 1, wherein said flow regulator is made of a silicon compound.

9. The device according to claim 1, wherein said flow regulator comprises a plurality of flow regulators aligned axially.

10. The device according to claim 1, wherein the said cap is made of lightweight plastic and has a slightly smaller transverse cross-section than said flow passage of said casing, thus permitting said cap to slide axially within said flow passage of said casing.

11. The device according to claim 1, wherein said casing has fluid flow calibration marks disposed thereon, said cap registering with the calibration marks to indicate the fluid flow through the device.

12. The device according to claim 1, wherein said flow regulator is calibrated to permit a particular viscosity of fluid to flow therethrough within a predetermined range of flow rates.

13. The device according to claim 1, wherein said flow regulator is calibrated for at least one of a 5% Dextrose solution, Lactated Ringers solution, and an 0.9% Sodium Chloride solution.

14. The device according to claim 1, wherein the outside surface of said casing has a marking of calibrated flow rate of at least one of a 5% Dextrose solution, Lactated Ringers solution, and an 0.9% Sodium Chloride solution.

15. The device according to claim 1, wherein the outside surface of said casing has marking to indicate a particular solution to which the device has been calibrated.

16. The device according to claim 1, wherein said flow passage, said flow regulator, and said cap all have circular cross-sections.

* * * * *